(12) United States Patent
Rom

(10) Patent No.: US 8,301,250 B2
(45) Date of Patent: Oct. 30, 2012

(54) INTELLIGENT CONTROL SYSTEM FOR ADAPTIVE CARDIAC RESYNCHRONIZATION THERAPY DEVICE

(76) Inventor: Rami Rom, Or Akiva (IL)

( * ) Notice: Subject to any disclaimer, the term of this patent is extended or adjusted under 35 U.S.C. 154(b) by 515 days.

(21) Appl. No.: 12/667,236

(22) PCT Filed: Jul. 17, 2007

(86) PCT No.: PCT/IL2007/000900
§ 371 (c)(1),
(2), (4) Date: Dec. 30, 2009

(87) PCT Pub. No.: WO2008/010220
PCT Pub. Date: Jan. 24, 2008

(65) Prior Publication Data
US 2010/0145402 A1    Jun. 10, 2010

Related U.S. Application Data

(60) Provisional application No. 60/807,513, filed on Jul. 17, 2006.

(51) Int. Cl.
*A61N 1/365* (2006.01)
(52) U.S. Cl. ............................................................. 607/9
(58) Field of Classification Search ........................ 607/9
See application file for complete search history.

(56) References Cited

U.S. PATENT DOCUMENTS

| | | | |
|---|---|---|---|
| 4,291,699 A * | 9/1981 | Geddes et al. | 607/6 |
| 5,251,626 A * | 10/1993 | Nickolls et al. | 607/14 |
| 5,800,467 A * | 9/1998 | Park et al. | 607/17 |
| 6,058,328 A * | 5/2000 | Levine et al. | 607/14 |
| 6,242,988 B1 * | 6/2001 | Sarpeshkar | 331/111 |
| 7,200,435 B2 * | 4/2007 | Ricci et al. | 607/9 |
| 7,280,989 B1 * | 10/2007 | Hoppensteadt et al. | 706/30 |
| 7,657,313 B2 * | 2/2010 | Rom | 607/17 |
| 2002/0103512 A1 * | 8/2002 | Echauz et al. | 607/9 |
| 2003/0158587 A1 * | 8/2003 | Esteller et al. | 607/45 |
| 2007/0129764 A1 * | 6/2007 | Burnes | 607/18 |

* cited by examiner

*Primary Examiner* — Carl H Layno
*Assistant Examiner* — Jeremiah Kimball

(57) ABSTRACT

An adaptive CRT control system that achieves optimal AV delay and VV pacing intervals associated with temporal patterns of stroke volumes that represent internally the heart conditions is disclosed. The adaptive CRT control system includes: (a) at least two implanted electrodes in patient heart and at least additional one hemodynamic sensor able to indicate the stroke volume heartbeat after heartbeat; (b) an input pre processing stage synchronizer priority classifier that synchronize on the sensed atrial event, classify heart conditions and associate the learned optimal pacing intervals according to prioritized operational modes and learning schemes; (c) a learning module that with the input stage synchronizer priority classifier processes the inputs of the implanted electrodes and hemodynamic sensor and using a reinforcement learning scheme learns to achieve and to associate optimal pacing intervals at each heart condition with temporal patterns of stroke volumes; (d) an algorithmic micro-controller module that supervises the learning module and control a pulse generator module, and (f) a pulse generator that delivers therapeutic stimulation to the patient heart.

11 Claims, 7 Drawing Sheets

INTELLIGENT CONTROL SYSTEM FOR ADAPTIVE CARDIAC RESYNCHRONIZATION THERAPY DEVICE

CROSS-REFERENCE TO RELATED APPLICATIONS

The present application claims the benefit of priority to U.S. Provisional Patent Application Ser. No. 60/807,513 filed Jul. 17, 2006, entitled "INTELLIGENT CONTROL SYSTEM FOR ADAPTIVE CARDIAC RESYNCHRONIZATION THERAPY DEVICE;" the aforementioned application is incorporated herein by this reference.

FIELD OF THE INVENTION

The present invention relates to implanted cardiac pacemakers and defibrillators and more specifically to cardiac resynchronization therapy devices, neural network architectures and learning schemes and intelligent control systems.

BACKGROUND OF THE INVENTION

In previous patent application 60/685,464, by the same inventor, a neural network was disclosed that learns to associate VA interval with temporal patterns of a hemodynamic sensor. The associated VA interval was used to replace the natural sensed atrial events during atrial fibrillation episodes. In addition, the patent suggested another preferred embodiment wherein the associated VA interval would replace the sensed atrial event during normal sinus rhythm as well as long as the associated signal is valid.

The associated VA interval with a temporal pattern of a hemodynamic sensor, cited above, is a prediction method based on learning to associate an input signal with another preceding input signal pattern. The associative learning paradigm uses timing causality instead of a physical model for solving the underlying system dynamics. The learning paradigm associates a solution, for example a VA interval with a temporal pattern of a hemodynamic sensor that reflects the physical system behaviour without the need to know and describe the detailed initial state, forces and interactions that determine the cardiac muscle behaviour. Hence, it may be used as an alternative paradigm to approaches like Newtonian equations of motion in classical mechanics or finite elements calculations of the electromechanical behaviour of the heart that determines the system dynamics by modelling the underlying physical forces and interactions. The advantage of the associative learning paradigm according to the system sensed parameters is that with a complex system, that might have unknown internal structure and internal states, associative learning can produce accurate predictions for the system dynamics, while solving a Newtonian equation based on modelling the physical system might be too complex and at times impossible since not all relevant internal system states are known and can be taken into account. In addition with associative learning, the time intervals can be large compared to regular propagation methods. In addition to the general argument given above there are two additional reasons to prefer working with an associated VA interval according to a hemodynamic sensor signal in cardiac pacemakers which are: a superior behaviour of a hemodynamic sensor comparing to the local weak intracardiac electrogram and sensitivity to noise sources that are accumulated in the sensed signals, digitized and processed might be reduced by neural network processing.

CRT is an established therapy for patients with congestive systolic heart failure and intraventricular electrical or mechanical conduction delays, Ellenbogen, Kay and Wilkoff, "Device Therapy for Congestive Heart Failure", Elsevier Inc. (USA), 2004. CRT is based on synchronized pacing of the two ventricles according to the sensed natural atrium signal that determines the heart rhythm. The resynchronization task demands exact timing of the heart chambers so that the overall stroke volume is maximized for any given heart rate (HR). Optimal timing of activation of the two ventricles is one of the key factors in determining cardiac output. The two major timing parameters which are programmable in a CRT device and determine the pacing intervals are the atrioventricular (AV) delay and interventricular (VV) interval.

Zachary I. Whinnett et al in "Hemodynamic effects of changes in AV and VV delay in cardiac Resynchronization Therapy show a consistent pattern: analysis of shape, magnitude and relative importance of AV and VV delay", Heart published online, 18 May 2006, doi:10.1136/hrt.2005.080721, studied importance of the AV delay and VV intervals optimization in CHF patients. The authors concluded that changing the AV and VV delay result in a curvilinear and reproducible acute blood pressure response. This shape fits very closely to a parabola, which may be helpful in designing a streamline clinical protocol to select optimal AV and VV delay.

In the present invention the adaptive CRT device control system to an intelligent control system that learns to associate therapeutic actions with input temporal patterns e.g. patterns of stroke volumes that are used for internal representation of heart conditions is further developed. Temporal patterns of stroke volumes are used to improve a reinforcement learning scheme, to classify heart conditions and to associate with the reinforced learning scheme and/or each particular heart condition the learned optimal system therapeutic actions.

DETAILED DESCRIPTION OF THE PRESENT INVENTION

In the present invention two components of an intelligent control system are defined. The first component has at least two operational modes, the first being sensed and associative-optimal, with a built-in preference to operate in the associative-optimal mode, and the second ingredient an internal representation of the system environment that allows the system to classify the environmental condition and associate with it the learned optimal system actions.

Figure 1:
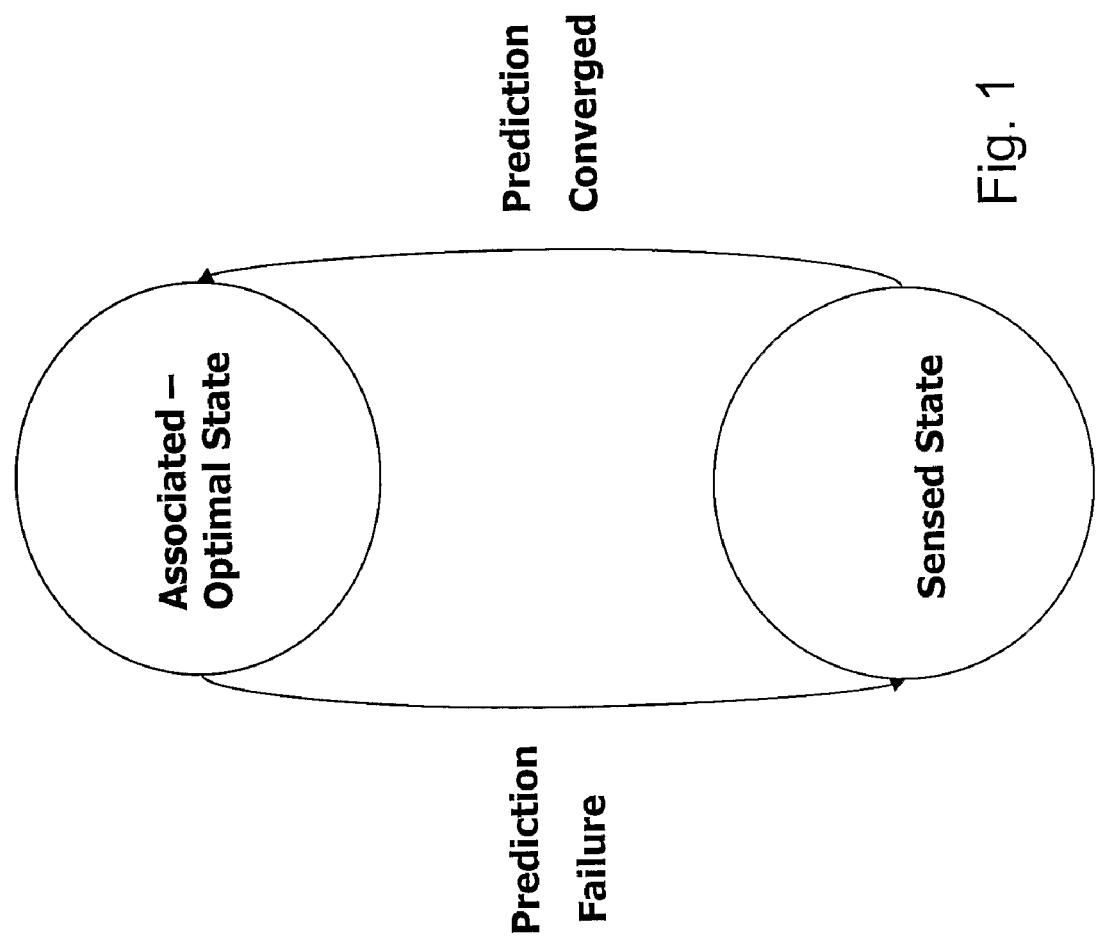
FIG. 1 is a state machine of intelligent controller according to this invention with associative-optimal and sensed state.

The two operational modes are shown in a state machine diagram in FIG. 1 to which reference is now made. In the first mode direct sensing of the environment is preformed and the machine controller operates according to the sensed value. In the second mode the intelligent controller system has learned to associate a value with the temporal patterns of the sensors using a neural network module (or other learning module) and operate according to the associated value replacing the direct sensed value.

An example for the potential benefit of control system operating in an associative-optimal state was described U.S. Provisional Patent Application, 60/685,464, by the same author in which a method for ventricular pacing during Atrial Fibrillation (AF) episodes was disclosed. AF is the most common cardiac rhythm disorder and it affects an estimated 2.3 million adults in the United States, the majority of whom are over age 65. AF can lead to stroke, tachycardia-induced cardiomyopathies, and congestive heart failure. According to the presently discussed approach the pacemaker device controller learns to associate the VA interval with a temporal pattern of a hemodynamic sensor during normal sinus rate. When the AF is detected the control system switches to operate in the associated VA interval state in which it replaces the sensed atrial event rendered unreliable during AF with the associated VA interval that reflects the ventricle function as seen through the temporal pattern of hemodynamic sensor. The sensed and associative-optimal states will be described in more detail further on.

The second component of an intelligent control system according to the present invention is its ability to classify the environmental condition and to learn the optimal system actions from the environment responses to the system actions for each condition. In the present invention temporal patterns of implanted hemodynamic sensors are used to represent internally in the controller the heart conditions. The intelligent control system of the present invention is an improvement of the reinforcement-learning scheme disclosed in a previous patent application by the same author, WO 2005/007075, by introducing an improved reinforcement learning scheme described below and by adding a classification scheme and long term memory of heart conditions through an input pre-processing stage synchronizer-priority-classifier unit.

Figure 6:
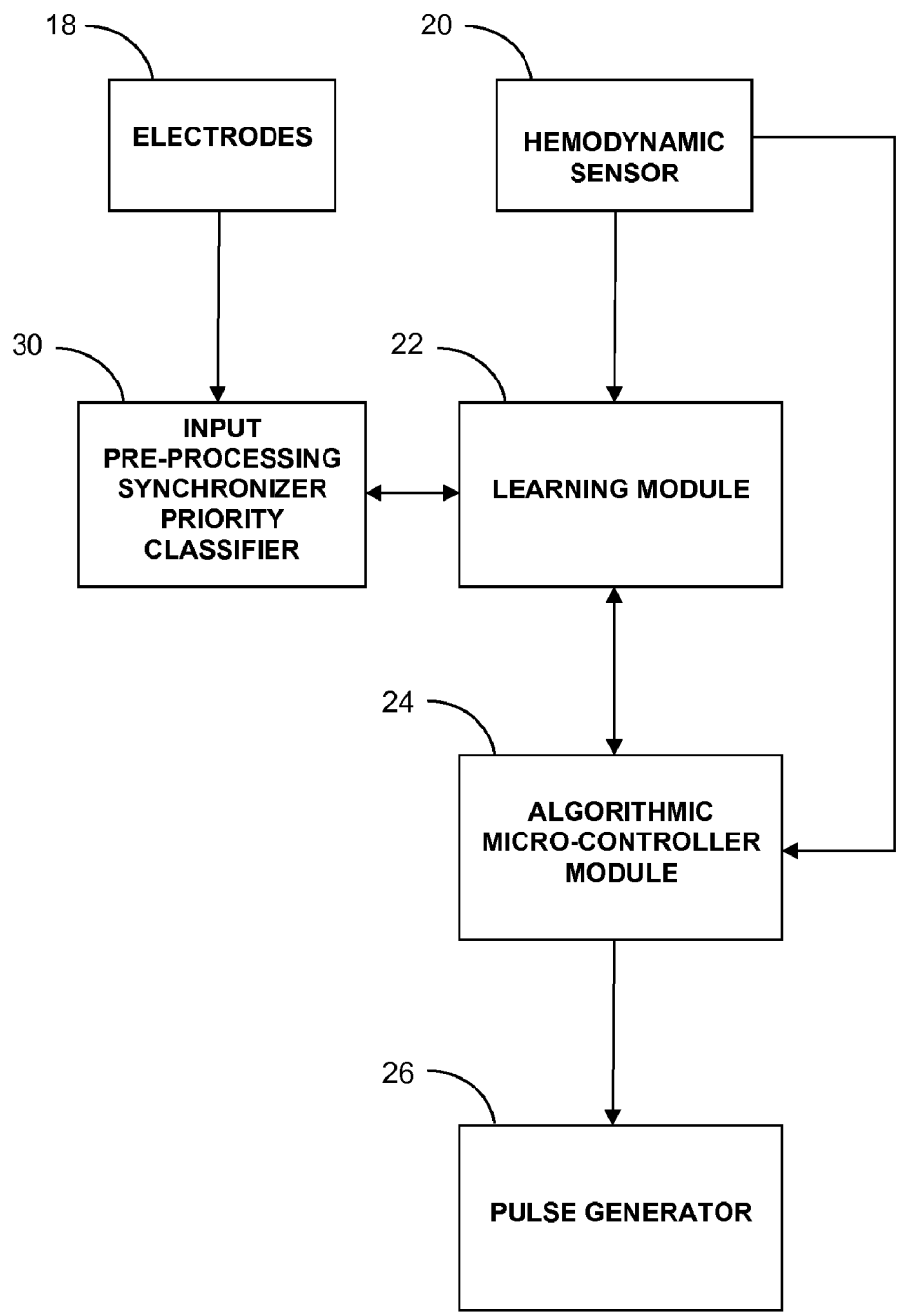
FIG. 6 is a schematic presentation of an embodiment of an adaptive CRT control system.

FIG. 6 shows an embodiment of an adaptive CRT control system, which, as noted, is an improvement to the system disclosed in the aforementioned WO 2005/007075 application (now U.S. Pat. No. 7,657,313). The adaptive CRT control system comprises at least two heart-implantable electrodes 18; at least one hemodynamic sensor 20; a learning module 22; an algorithmic micro-controller module 24; and a pulse generator 26, adapted to deliver therapeutic stimulation to a patient heart. The adaptive CRT control system further comprises an input pre-processing stage synchronizer priority classifier 30 adapted to: (a) synchronize a sensed atrial event; (b) classify heart conditions; and (c) to associate learned optimal pacing intervals according to prioritized operational modes and learning schemes.

Learning module 22 operates in conjunction with input pre-processing stage synchronizer priority classifier 30 and is adapted to process inputs of electrodes 18 and the hemodynamic sensor 20—and, using a reinforcement learning scheme, is configured to learn to achieve and to associate optimal pacing intervals at each heart condition with temporal patterns of stroke volumes. Algorithmic micro-controller module 24 is configured to supervise learning module 22 and to control pulse generator 26.

Reinforcement Learning with a Repetition Parameter

With complex cardiac function dynamics one can expect that with changing pacing parameters, AV delay and VV interval, applied by the adaptive CRT controller the heart will reach a new steady state only after several cardiac cycles depending on various variables such as the heart rate, blood pressure, pre-load volumes, metabolic need and general behaviour depending not only on the parameters of the current cardiac cycle but also on longer time scale of several cardiac cycles. Information based only on the current cardiac cycle might not suffice to predict the optimal behaviour and steady state achieved in the next several cardiac cycles. The cardiac system response to a change in pacing intervals will occur typically after approximately 10 heart beats. The reinforcement learning scheme presented in WO 2005/007075 is a greedy gradient search type scheme that endeavours to achieve for each cardiac cycle a higher stroke volume as a function of the changed AV and VV pacing intervals and does not take into account the longer response time of the cardiovascular system.

In the present invention a programmed parameter, $N_{repetition}$, defines the number of cardiac cycles that are paced repeatedly with each new configuration of AV and VV before another change is made within the reinforcement-learning scheme. During the $N_{repetition}$ cardiac cycles an averaged stroke volume is calculated and used in the RL scheme replacing the stroke volume calculated only at the first cardiac cycle after transition as described in a previous patent application WO 2005/007075.

Guided Reinforcement Learning (GRL) Scheme

In the aforementioned application WO 2005/007075, a pacing register holds the values of the optimal pacing AV delay for the right and left ventricles. During the adaptive CRT mode the value stored at the pacing register is changed according to the timing relation between the integrate and fire (I&F) neuron firing time and the value that is stored at each cardiac cycle. When the I&F neuron fires before the stored value, the pacing register value is decremented and when the firing occurs after the stored value it is incremented. The distribution of firing times is evenly spaced around the stored value in the pacing register but it is random in the sense that at for a particular cardiac cycle it is not known a priori if it will occur before or after the stored value. Concurrently, the synaptic weights that drive the I&F neuron are changed by a greedy type learning rule presented in details in WO 2005/007075 that drives the pacing interval stored at the pacing register to the optimal value that generates the maximum stroke volume value beat after beat on line. Hence the reinforcement learning scheme has no ability to use accumulated learning such that the search for the optimal AV delay and VV intervals will be more efficient and converge faster to the optimal values at each heart conditions with accumulated experience.

In the present invention the GRL preferred state uses a neural network prediction based on temporal patterns of stroke volume values obtained from a hemodynamic sensor to modify locally and selectively the synaptic learning rate parameters as will be elaborated infra. Summarized differently, the stroke volume values obtained from a hemodynamic sensor are sampled and processed and then the values are stored as a temporal pattern that may be further used as input to a neural network that learns to associate with the stroke volume temporal pattern that internally represents a heart condition with a pacing interval pattern part of a guided reinforcement learning scheme.

Figure 2B:
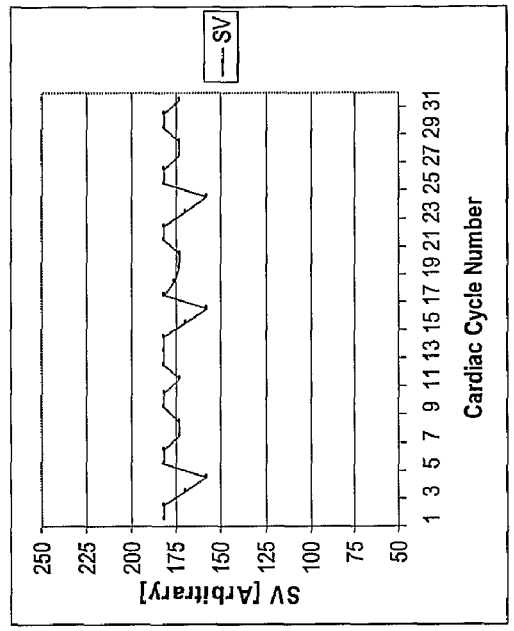
FIGS. 2 A-E shows the stroke volumes patterns at different simulated heart conditions.
Figure 2A:
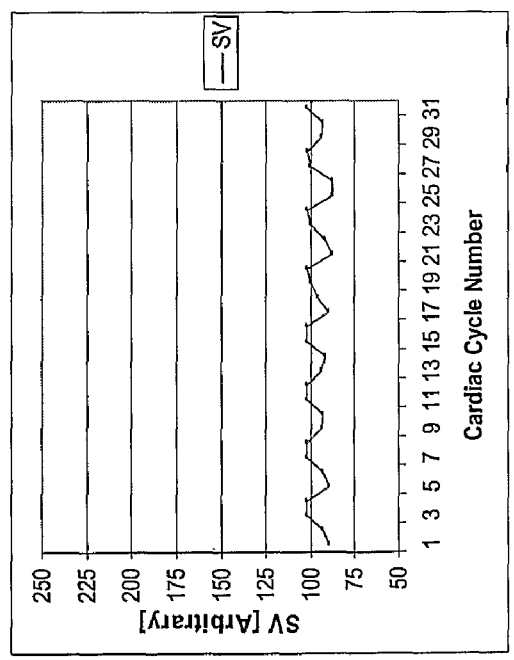
Figure 2C:
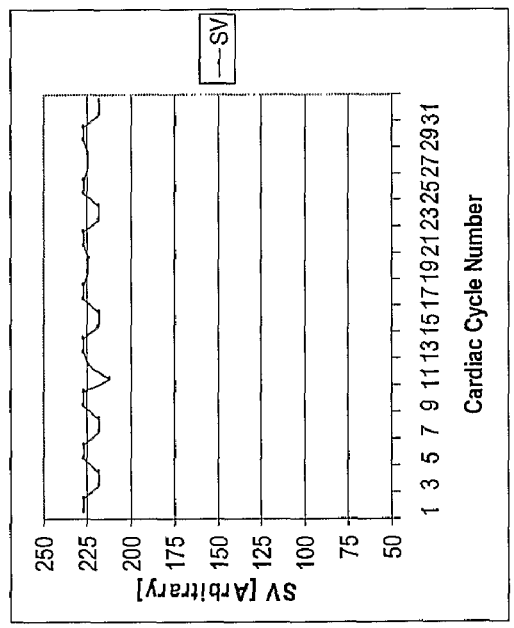
Figure 2E:
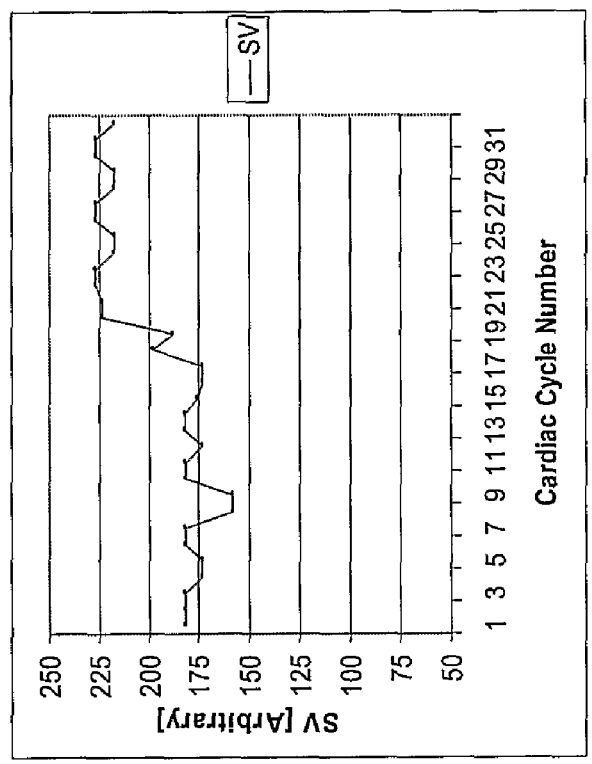
Figure 2D:
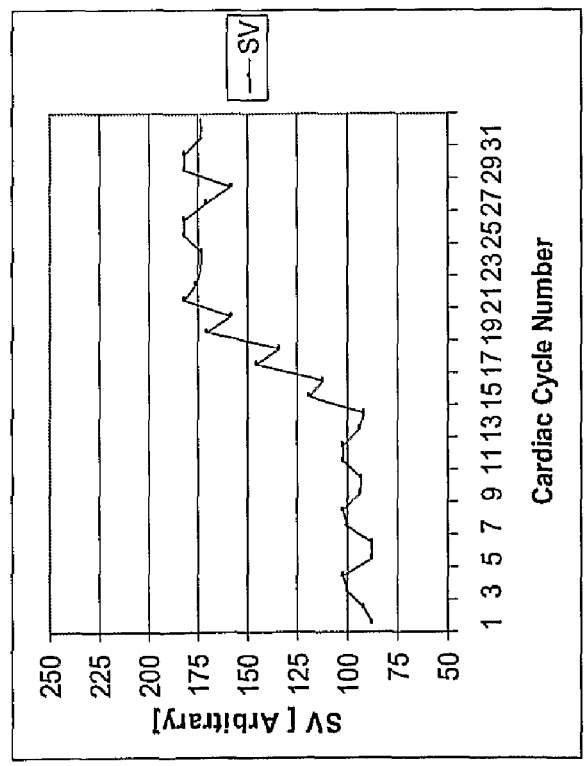

FIGS. 2A-E, whereto reference is now made, show an example of five patterns of stroke volumes in a simulation in different heart conditions. In FIG. 2A the simulated heart rate was 70 beat per minute (BPM), FIG. 2B the simulated heart rate was 100 BPM and FIG. 2C the simulated heart rate was 130 BPM. FIG. 2D and FIG. 2E show the stroke volumes during a transition from 70 BPM to 100 BPM and from 100

BPM to 130 BPM respectively. FIGS. 2A-E show how the stroke volume patterns internally represent the heart condition as well as transition periods from one heart condition to another.

Figure 3:
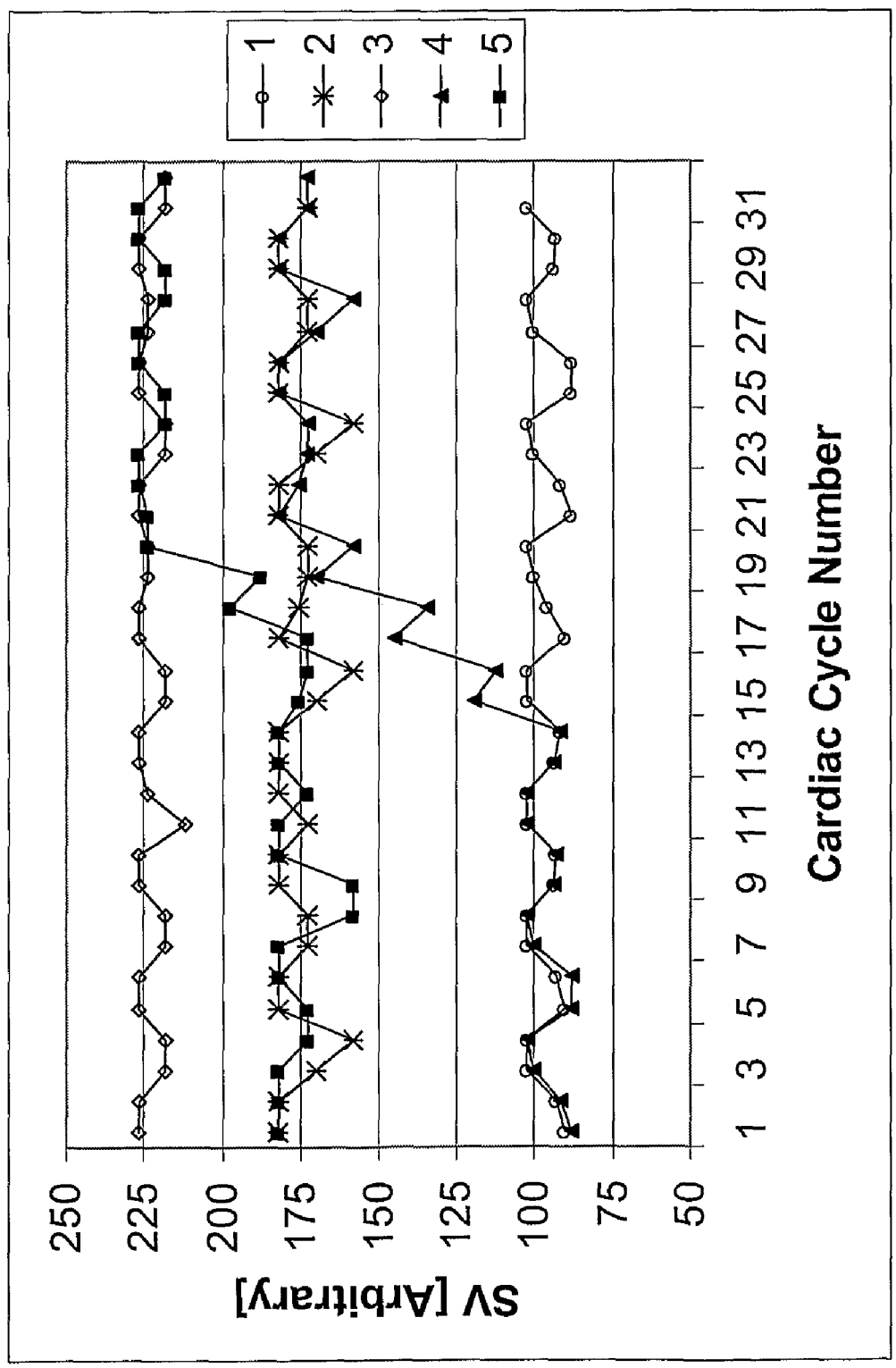
FIG. 3 shows the stroke volumes patterns at different simulated heart conditions with overlay plot.

Referring now to FIG. 3, which is an overlay of the stroke volume patterns as were presented in FIGS. 2A-E, showing the ability of the stroke volume patterns to represent of the different heart conditions internally in the controller device. Note for example how plots number 4 and 5 in FIG. 3 show the transition from steady stroke volumes at 70 BPM to a higher value at 100 BPM and to even higher values at 130 BPM.

With the GRL scheme the stored stroke volumes are sampled in each cardiac cycle and the last 8, 16 or more cardiac cycles stored values are used as input pattern to a neural network architecture built with a similar building blocks described in U.S. Provisional Patent Application, 60/685,464, by the same author. The neural network generates a prediction of the learned optimal pacing parameter based on the input pattern. A prediction hit count rate function is calculated where a hit is defined when the delivered pacing interval falls in a predefined time window in the vicinity of the neural network predicted value. When the hit count rate is above a threshold transition to the GRL state from the RL state occurs. When the hit count rate is below a threshold transition to a FAIL GRL state will occur. In RL, GRL and FAIL GRL states the RL scheme of the adaptive CRT device as presented in previous patent application of the author "Adaptive CRT Systems", WO 2005/007075, January 2005, is implemented and an improvement suggested here is to use a local and selective learning rate parameter adjustable in each synapse in each synapse module.

The guided RL scheme may take into account either the random process of the I&F neuron firing times described above, the pacing intervals patterns which are associated with a heart condition through the stored temporal pattern of stroke volumes, or both parameters. The guided RL scheme can be as follows; when the I&F neuron fires early and the associated pacing interval is also below the stored pacing interval or both are above the stored value, the pacing register is incremented or decremented with no changes relative to the scheme depicted in WO 2005/007075. When the I&F neuron firing time and the associated pacing interval generate contradicting predictions we will in one preferred embodiment prefer the associated value and this algorithm will be referred here as the full guided RL scheme and in another preferred embodiment we will select randomly between the I&F firing time and the associated pacing interval value and we will refer to this choice here as the partial guided RL scheme.

The advantage of the guided RL scheme as laid out supra is that adaptations are not based solely on one cardiac cycle at a time but also on the accumulated learned behavior of several cardiac cycles and since the associated patterns of stroke volumes reflects the underlying heart condition the guided RL scheme is expected to improve the performance with accumulated experience.

Local and Selective Synaptic Learning Rate Parameters

In "Adaptive Cardiac Resynchronization Therapy Device Based On Spiking Neurons Architecture and Reinforcement Learning Scheme", Rom et. al., IEEE-TNN, Vol 18, Number 2, 542-550, March 2007, we suggested using a dynamic synaptic learning rate parameter as a strategy to allow both synaptic stability and plasticity. With the present invention this approach is continued further and we allow the synaptic learning rate parameter to be changed in each synapse, $\lambda_{ij}$, selectively according to the CRT state, the synapse local activation state and a prediction hit count rate function. When the synapse is highly activated and the prediction hit count is also high, meaning the synapses is highly effective in driving the postsynaptic I&F neuron, the local learning rate is decreased and hence only this specific synapse gains stability. The selective local learning rate adjustments result in better stability and prevent losing an already learned knowledge by new input patterns. Note also that with a smaller learning rate parameter the system is still adaptive and still maintains a reduced plasticity. In addition, new patterns that will excite other synapses in the middle layer will be processed with a higher plasticity that with the same stabilization mechanism described here may become new stable learned patterns.

The local selective learning rate parameter calculation is implemented in each synapse with a local register called excite. When the post neuron spike occurs at a Hebb state and at the correct target time the excite register is incremented. When the post neuron spike occurs at a pre-Hebb or post-Hebb state the excite register is decremented. According to the value of the local excite register in each synapse the learning rate parameter is adjusted. The maximal value of the excite register is 31. The local learning rate parameter is inversely proportional of the excite register and the step size of changes of the synaptic weight are proportional to the learning parameter value. The Hebb, pre-Hebb and post-Hebb are local synaptic states that record at each synapse in the neural network architecture the state the synapse state machine was at the time of the post neuron spike occurred. The time is measured internally in each synapse relative to the pre-synaptic excitation.

Accumulated Knowledge and a Learning Curve

We define an accumulated knowledge function of the neural network as the sum of the inverses of all the local synaptic learning rates.

$$\text{Accumulated Knowledge} \sim \Sigma_{ij} \, 1/\lambda_{ij} \qquad \text{Eq. (1)}$$

When the neural network converges and the predicted values match the delivered pacing parameters the local learning rates become small and the accumulated knowledge function is maximal. When new patterns are sensed and the system prediction is off the target, the CRT state will switch to FAIL GRL state, the predicted hit count rate will lessen and the learning rate parameters will increase and hence the accumulated knowledge function will show a decrease. Hence a growth in the calculated accumulated knowledge is a measure of learning and a decrease is a measure of losing knowledge already acquired due to new input patterns.

The local selective adjustable synaptic learning rate parameters are used hence to define a qualitative and quantitative measure of accumulated knowledge acquired by the neural network and its changes over time gives a measure of learning performed by the neural network.

Long Term Memory of Heart Conditions

The reinforcement-learning scheme we presented in WO 2005/007075 is a greedy type algorithm that tries to reach higher stroke volume value at each cardiac cycle on line. Such a greedy algorithm does not have a long-term memory. We included in WO 2005/007075 a long-term memory of heart conditions by adding a pre-processing input stage temporal synchronizer decoder. The temporal synchronizer decoder excites a subgroup of synapses selectively in the middle layer according to predefined heart rates ranges and hence a learned solution with a specific heart range is stored in the optimal steady state synaptic weights and hence the architecture has a long term memory of optimal solutions for predefined heart conditions (characterized by the average heart rate ranges).

With the present invention, heart conditions are represented internally by their stroke volumes and temporal patterns and a pre-processing stage synchronizer-priority classifier learns to associate with the temporal pattern of stroke volumes a subgroup of synapses in the middle layer that encode learned optimal pacing intervals. Hence the neural network has a learned long term memory of classified heart conditions that are encoded in the neural network synaptic weights during operation in real time and on line as described further below.

The Synchronizer-Priority-Classifier (SPC) Unit

The present invention uses an input pre-processing stage synchronizer-priority classifier for an adaptive cardiac resynchronization therapy device. The SPC pre-processing input stage includes a learning scheme that learns to classify different heart conditions according to the sampled and stored stroke volumes temporal patterns associated with the learned optimal pacing solutions.

The SPC unit includes a temporal synchronizer, a temporal pattern recognition neural network, and a state machine that defines the CRT operational state.

According to one example, the learned optimal solutions may be activated by the SPC unit through the selective excitation of subgroups of middle layer synapses and accordingly the right and left ventricles are stimulated by the adaptive CRT device controller. Concurrently, only the synapses excited by the SPC unit in the middle layer will be trained to associate with the current heart condition, as seen by the temporal patterns of stroke volumes, the optimal pacing intervals that can be viewed as optimal instructions for the controller to stimulate the heart. Hence the present invention's SPC unit enables the adaptive CRT device controller to classify the heart condition according to internal temporal pattern representation of the heart condition and to associate and schedule the next optimal instructions according to the heart condition and a priority state machine described in the following and hence it operates in addition as a built-in program sequencer that schedules the learned optimized instructions associated with optimal performance for the adaptive CRT device.

Temporal Pattern Recognition and Association Scheme

The temporal pattern recognition spiking neurons architecture we use in the SPC unit has three functional stages. The first stage is a pre-processing layer of the hemodynamic sensor data by a temporal synchronizer. The synchronizer selectively excites an array of dynamic synapses in the middle layer. The middle layer has 200 dynamic synapses that are arranged in 10 rows with 20 synapses in each row. The temporal synchronizer excites selectively dynamic synapses at each row according to the value of the input hemodynamic sensor impedance signal. In addition the temporal synchronizer excites each row at a predefined different delay time measured from the triggering sensed ventricular event. Hence the temporal synchronizer perform pre-processing of the input signal by selectively exciting different dynamic synapses groups in the middle layer according to the varying heart conditions. At the output layer there are typically sixteen integrate-and-fires (I&F) neurons that receive the postsynaptic responses excitations (PSR) from the dynamic synapses and a control unit that manages the learning rule performed concurrently in the middle layer dynamic synapse. The I&F neurons are trained to fire at a target time which can be for example delivered AV delay obtained by the RL at all heart conditions. The neural network supervised learning rule is described below. The sixteen I&F neurons are trained to fire at the target time and a fuzzy average result with a hit count rate membership function (described in more details further below) for each I&F neuron is calculated as the final associated AV interval of the neural network. The fuzzy average calculation increase the accuracy and the ability to filter noisy signal with the neural network and plays additional roll in the control task as will be described in more details below.

The dynamic synapses of the pattern recognition adjust an internal time delay parameter, $\tau_{ij}$, measured from the presynaptic excitation to the postsynaptic response (PSR). The learning scheme is one of supervised learning wherein the target time is the delivered AV delay for each ventricle. Hebbian learning is performed at each synapse module concurrently according to the relative timings of the pre- and postsynaptic pulse inputs.

In each cardiac cycle the synapses that were excited by the temporal synchronizer starts incrementing an internal counter. When the firing time of the I&F neuron occurs before the internal time delay parameter expires, the synapse state is stored as a Pre Hebb state. When the firing time occurs within a is predefined time interval, $\Delta$, just after the expiration of the synapse state is stored as a Hebb state. When the firing time of the I&F neuron occurs later the synapse state is stored as a Post Hebb state. The stored Hebb states are used locally in each synapse for the calculation of the activity and effectiveness of each synapse as described in sub section E below.

The postsynaptic response (PSR) is emitted by the synapse in the Hebb state and the contributions from all the synapses in a subgroup are accumulated by integrate-and-fire (I&F) neurons.

Hit Count Rate Membership Function

Figure 4:
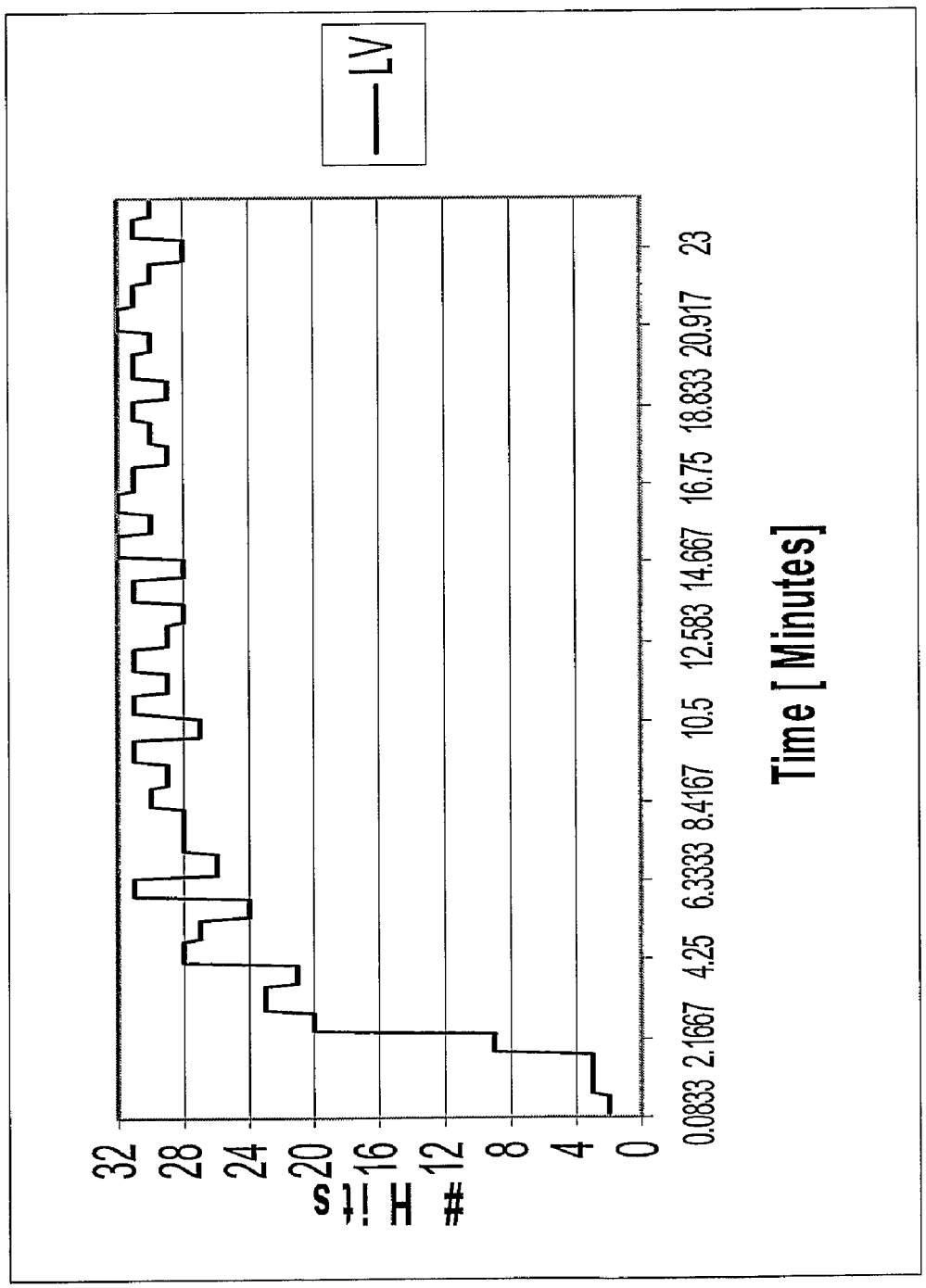
FIG. 4 shows the hit count rate membership function.

We define a hit count rate at the target time of the I&F neuron as a membership function. The membership function is a measure of the "truth" of a variable. With the spiking neurons the relevant variable is the I&F neuron firing time and the membership function is the hit count rate at the learned target. The hit count rate function is calculated as the number of hits of the I&F neuron spikes in a time window of 10 milliseconds in the vicinity of the learning time target in a time frame of 32 cardiac cycles. The maximal value for the hit count rate membership function is 32 when the I&F neuron fires at the correct target time every cardiac cycle and the membership function vanishes when the I&F neuron fires out of the time window during all cardiac cycles in a time frame. The hit count rate membership function is shown in FIG. 4. After five minutes of simulation the I&F neuron learns to fire at the programmed time and the number of hits at the target time converging to the maximal value in a time frame of 32.

The Association Scheme

In summary the temporal pattern recognition spiking neural network architecture described above with a hit count rate membership function calculation for each I&F neuron in the output layer is trained to associate the learned AV delay and VV interval obtained by RL scheme with the temporal pattern as shown in FIG. 3 and using hit count rate membership function shown in FIG. 4 to which reference is now made. The predicted AV delay is calculated according to equation 2 below $$\text{Predicted AV} = \Sigma f(Ti) * Ti / \Sigma f(Ti) \qquad \text{Eq. (2)}$$

Where f (Ti) is the hit count rate membership function calculated for each I&F neuron, Ti is the spiking neuron firing time measured relative to the sensed ventricle event in each cardiac cycle and the sum is taken over all the integrate-and-fire neurons.

The SPC Unit State Machine

Figure 5:
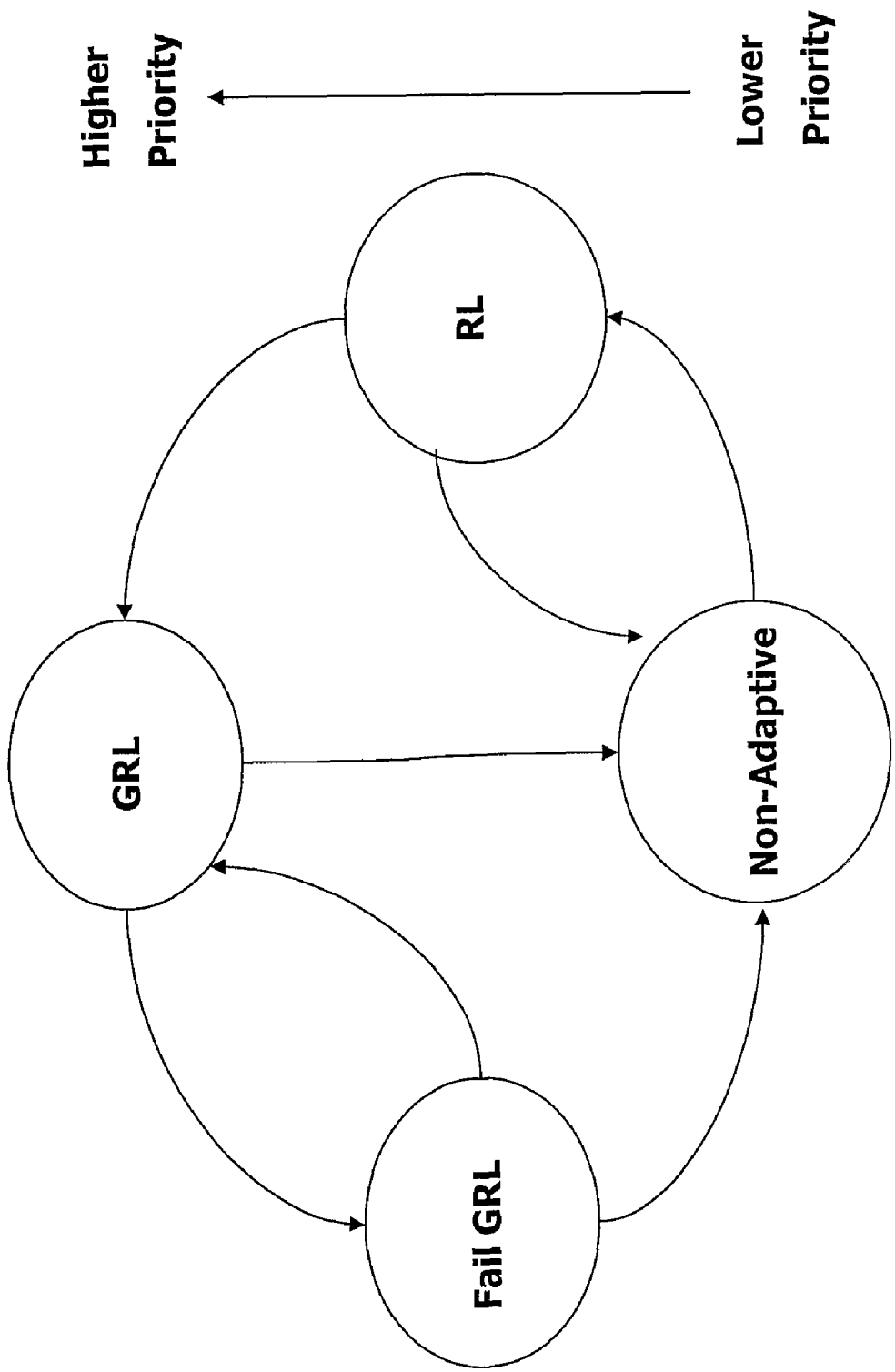
FIG. 5 shows the adaptive CRT control system according to the present invention with four states, non-adaptive CRT, Reinforcement Learning (RL), Guided Reinforcement Learning (GRL) and Fail GRL.

Reference is now made to FIG. 5 that shows a state machine diagram of the adaptive CRT intelligent control system of the present invention. The finite state machine has four states that are characterized by the operational mode and the learning schemes executed in each state wherein the state machine has a built in priority.

Non-Adaptive CRT state

In the non-adaptive CRT state the CRT device uses the programmed AV delay and VV interval as the fixed pacing delays as in the case of prior art CRT devices. The input stage SPC excites the middle layer synapse after an atrial event is sensed and this is used as a synchronizing event each heartbeat. Next the SPC excites different subgroups of synapses selectively according to the average heart rate according to a predefined heart rate range decoder and in each subgroup of synapses each synapse is excited with a fixed predefined increasing time delay measured from the synchronizing atrial event. The middle layer is composed of dynamic synapses modules wherein learning is achieved by modifying the synaptic weights continuously during real time operation. The output layer is composed by two leaky integrate and fire neurons modules that accumulate postsynaptic responses from the middle layer synapses and together with the master controller manage the pacing of the right and left ventricles beat after beat. In the non-adaptive CRT state the middle layer synaptic weights are trained with a supervised learning scheme and the synaptic weights reach a steady state values that bring the output layer integrate and fire neurons to fire at the programmed AV delay and VV interval.

The input layer SPC unit use average heart rate calculated as the average time between adjacent atrial sensed signals to selectively excite a subgroup of the middle layer synapses at each heart rate range.

Typically there are predefined 5 ranges of heart rates, below 60 BPM, 60-80 BPM, 80-120 BPM, 120-140 BPM, beyond 140 BPM and for each range a different subgroup of middle layer synapses are excited and trained by the input stage synchronizer-encoder-sequencer unit.

Adaptive CRT Reinforcement Learning (RL) State

In the adaptive CRT RL state the middle layer synaptic weights are trained with a reinforcement learning scheme that was described in details in WO 2005/007075 and the synaptic weights reach steady state values that bring the output layer leaky integrate and fire neurons to fire at the optimal AV delay and VV interval according to responses from hemodynamic sensor that reflect the stroke volume dependence on the changing AV and VV delays. The RL scheme finds the maximum stroke volume on a bell shape curve as a function of pacing intervals at each heart condition and will track changes of the optimal pacing intervals as heart condition change.

In the RL state the SPC unit neural network is trained to associate the optimal pacing interval, i.e. optimal AV delay and VV interval, with input temporal patterns.

Adaptive CRT GRL State

In the adaptive CRT GRL state the learned predicted value of the SPC unit neural network is used to define a predicted hit count rate function defined similarly to the I&F neuron hit count rate function shown in FIG. 4. The success of the RL scheme AV delay and VV interval to match the SPC unit predictions is measured by the predicted hit count rate function and this measure is used as a transition criterion to and from the GRL state. In the GRL state the active synapses decrease their local learning rate parameters, which provides higher stability to the neural network based solution for the optimal AV delay and VV interval.

The SPC unit state machine described here has a built in preference to operate in the state that brings the best system performance, that of the adaptive CRT GRL state FAIL GRL State The FAIL GRL state aim is to allow the system to converge back to the preferred GRL state while the learning scheme remains one of Reinforcement Learning (RL), but since the SPC unit neural network prediction fails (predicted hit count rate is low) the local synaptic learning rate parameters of the active synapses are increased now and the neural network become more flexible to converge to new values of optimal AV and VV intervals.

Switching Criteria

Switching between the at least three or preferably four states occurs automatically back and forth during operation as part of the intelligent controller regular operation. The switching criteria are described below.

The switching from non-adaptive to the adaptive RL state is made according to convergence of the supervised learning scheme in the non-adaptive CRT mode. The integrate-and-fire neuron need to hit the target with a high hit count rate in an exemplary time frame of 32 cardiac cycles as shown in FIG. 4, meaning that the learning task in the non-adaptive mode is achieved.

The switching between adaptive CRT RL state back and non-adaptive CRT state is made according to predefined system failures that can be for example excessively short or long AV delay and or VV interval (crossing predefined limits), an excessively low hit count rate value or other failures such as a detected arrhythmia.

The switching from adaptive CRT RL state to adaptive CRT GRL state is made according to convergence of the SPC unit pattern recognition neural network learning task. The predicted hit count rate function has to surpass a predefined threshold value. The prediction hit count rate is calculated over a longer time. An exemplary period of 4 time frames may contain 128 cardiac cycles.

The switching back from adaptive CRT GRL state to non-adaptive CRT state is made according to predefined system failures that can be for example excessively short or long AV delay and or VV interval (crossing predefined limits), an excessively low hit count rate value or other failures such as a detected arrhythmia.

The switching from adaptive CRT GRL state to adaptive GRL-FAIL state is made when the predicted hit count rate is too low meaning that a new input temporal pattern is processed by the SPC unit.

The switching from GRL-FAIL state back to adaptive GRL state is made when the predicted hit count rate exceeds the predefined threshold meaning that the new input temporal pattern is learned now and associated with optimal values of AV delay and VV interval by the SPC unit.

The switching from GRL-FAIL state back to non-adaptive CRT state can be made, inter alia, according to a low hit count rate value that can be typically higher value then the value used in the other states. This higher value reflects higher sensitivity of the system to failures in the GRL-FAIL state to increase safety and fall back to the non-adaptive state, which is also a safety state of the Adaptive CRT controller.

Built-in Priority

In accordance with the present invention the intelligent control system has a built-in preference to operate in the GRL state as long as the conditions allow it (note the switching criterions section defined above). The system will always try to reach the GRL state and transitions to lower priority states will be recovered by the system repeatedly. In addition, the SPC unit state machine uses internal predictions of the optimal AV delay and VV intervals to define the switching criterions and to control the local synaptic learning rate parameters that change the plasticity of the neural network and it response to novel input temporal patterns. These two characteristics of the SPC unite state machine makes the control unit intelligent and patient specific.

Advantages of Implementing the Invention

Applying the system and method of the present invention, the improved guided reinforcement learning scheme and the adaptive CRT intelligent control system will be clinically beneficial for CHF patients treated with adaptive CRT devices.

The advantages of the invention are:
1. Guided reinforcement learning will improve the system performance using the accumulated experience of classifying heart conditions internally represented by temporal patterns of stroke volumes and associates the optimal AV and VV pacing intervals with each heart condition.
2. The SPC unit and specifically, operating in the adaptive CRT GRL state, will allow the system to supply the learned optimal pacing intervals, AV delay and VV intervals, associated with each heart condition and due to the built-in priority state-machine, the system will always try to reach the preferred GRL state repeatedly after each transition to lower priority states.
3. The SPC unit and specifically, operating in the adaptive GRL-FAIL state, will increase sensitivity to failures since in the GRL-FAIL state the temporal pattern recognition network had failed to detect a new input temporal pattern and now we give higher sensitivity threshold to RL scheme failures to deliver optimal AV delay and VV interval. The increased sensitivity in the FAIL-GRL state is important for safety of the implanted adaptive CRT system.
4. The SPC unit state machine uses internal predictions as the switching criteria between the different states which give the system flexibility to learn new input temporal patterns and gain stability with detected patterns using the local selective synaptic learning rate parameters.
5. The local and selective synaptic learning rate parameters are used to define a knowledge function as a qualitative and quantitative measure of the neural network. An increase in the knowledge function characterizes learning while decrease in this function is due to a loss of knowledge already acquired.

The invention claimed is:

1. An adaptive CRT control system intended to optimize AV delay and VV pacing intervals associated with temporal patterns of stroke volumes that internally represent the heart conditions, comprising:
   at least two implantable electrodes adapted to be implantable in a patient's heart and at least one hemodynamic sensor for indicating a stroke volume heartbeat after heartbeat;
   an input pre-processing stage synchronizer priority classifier adapted to synchronize a sensed atrial event, to classify heart conditions and to associate learned optimal pacing intervals according to prioritized operational modes and learning schemes;
   a learning module that with the input pre-processing stage synchronizer priority classifier is adapted to process inputs of the at least two implantable implanted electrodes and the at least one hemodynamic sensor, and using a reinforcement learning scheme, configured to learn to achieve and to associate optimal pacing intervals at each heart condition with temporal patterns of stroke volumes;
   a pulse generator adapted to deliver therapeutic stimulation to a patient heart; and
   an algorithmic micro-controller module configured to supervise the learning module and to control the pulse generator,
   wherein said adaptive CRT control system is configured to switch between a non-adaptive CRT mode, an adaptive CRT RL mode, an adaptive CRT GRL mode and a GRL-FAIL mode, wherein according to the operational mode said control system is adapted to deliver an optimal AV delay and VV interval biventricular pacing to a congestive heart failure patient.

2. A system as in claim 1, wherein each new AV delay and VV intervals values are delivered repeatedly $N_{repetition}$ times and where an average stroke volume is calculated and according to the average stroke volume, synaptic weights are adapted to allow the system to reach a new steady state according to the new pacing intervals.

3. A system as in claim 1 wherein said control system has a built-in preference to operate in an adaptive CRT GRL mode preferred state and where after each transition to a lower priority state the system will try to re-attain higher priority states repeatedly.

4. A system as in claim 2, wherein the system is adapted to perform guided reinforcement learning in order to achieve optimal pacing intervals at all heart conditions wherein within a scheme of the guided reinforcement learning, local and selective synaptic weight learning rate parameters are changed in order to give flexibility to learn new input temporal patterns and gain stability with detected patterns.

5. A system as in claim 2, wherein the system is adapted to perform guided reinforcement learning in order to achieve optimal pacing intervals wherein updates of the pacing intervals are correlated with the associated AV delay and VV intervals obtained by a learning module association with the stroke volumes temporal patterns that internally represent the heart condition and wherein the learned optimal pacing intervals according to learned classification of heart conditions enable a long term memory of heart conditions and wherein for each heart condition the system learns to deliver optimal therapy.

6. A system as in claim 1, wherein a state machine of the input stage synchronizer priority classifier, operating in the adaptive GRL-FAIL state, increases the adaptive CRT control system sensitivity and increases operation safety.

7. A system as in claim 1, wherein said system is patient specific and provides intelligent control by having a built-in priority to operate in a preferred state, an input pre-processing stage that learns online to classify the patient condition according to internal temporal patterns extracted from the at least one hemodynamic sensor and learns to associate the delivered optimal therapy using a reinforcement learning scheme, and having local and selective adjustable learning rate parameters that define a knowledge function accumulated in the learning module.

8. A system as in claim 4, that has local and selective synaptic learning rate parameters and has a knowledge function that is defined as the sum of the local inverse learning rate parameter of all the synapses in the learning module wherein an increase in the knowledge function characterizes learning while a decrease in this function is due to a loss of previously acquired knowledge.

9. A system as in claim 1, wherein said learning module is a spiking neural network implemented in a hardware processor with extremely low clock frequency and dynamic power dissipation.

10. A method for delivering Cardiac Resynchronization Therapy to a congestive heart failure patient comprising the steps of:
    obtaining a continuous signal from at least one hemodynamic sensor monitoring at least one hemodynamic parameter of said patient;

processing said continuous signal using an algorithmic micro-controller module and a learning module, wherein said learning module is adapted to carry out adaptive learning in connection with said at least one hemodynamic sensor and said adaptive learning is controllable and supervisable by said algorithmic micro-controller module;

delivering therapeutic stimulation by a delivery module in response to said processed signal, wherein said delivery module is controlled by said algorithmic micro-controller module, wherein said method further comprises:

programming initial atrioventricular (AV) delay parameters and interventricular delay (VV) interval parameters of said algorithmic micro-controller module;

providing pacing in a non-adaptive CRT mode where pacing is provided according to the initial programmed AV delay and VV interval parameters;

switching to an adaptive CRT RL mode wherein said AV delay and VV interval change dynamically using a reinforcement learning scheme in order to achieve optimal hemodynamic performance as sensed by the hemodynamic sensor;

learning to associate the AV delay and VV interval with temporal patters of stroke volumes extracted and stored beat after beat from the hemodynamic sensor and used as internal representation of heart conditions for the learning module;

using said associated pacing intervals to guide the reinforcement learning scheme;

switching to an adaptive CRT GRL mode wherein said AV delay and VV interval change dynamically using a reinforcement learning scheme wherein the local and selective synaptic weights of activated synapses are reduced to give stability to the neural network;

switching to GRL-FAIL mode whenever a classification scheme according to the temporal patterns of stroke volumes fails; and switching back to the non-adaptive CRT mode whenever the AV delay or VV interval crosses predefined high or low limits, or a sensor failure, or any other system failure is detected.

11. A method as in claim 10, further comprising the step of switching again to an adaptive CRT GRL mode when learning to associate the optimal pacing intervals, AV delay and VV interval, is again converged.

* * * * *